United States Patent
Kubo et al.

(10) Patent No.: US 7,135,443 B2
(45) Date of Patent: Nov. 14, 2006

(54) SURFACTANT COMPOSITION

(75) Inventors: Makoto Kubo, Wakayama (JP);
Kazuhiro Iitaka, Wakayama (JP);
Yohei Kaneko, Wakayama (JP);
Tomoko Uchiyama, Wakayama (JP);
Yasuhiro Doi, Wakayama (JP)

(73) Assignee: Kao Corporation, Tokyo (JP)

( * ) Notice: Subject to any disclaimer, the term of this patent is extended or adjusted under 35 U.S.C. 154(b) by 158 days.

(21) Appl. No.: 10/829,167

(22) Filed: Apr. 22, 2004

(65) Prior Publication Data

US 2004/0266647 A1 Dec. 30, 2004

(30) Foreign Application Priority Data

Apr. 23, 2003 (JP) .............................. 2003-117938
Oct. 17, 2003 (JP) .............................. 2003-357180

(51) Int. Cl.
C11D 1/83 (2006.01)
C11D 3/20 (2006.01)
A61K 8/34 (2006.01)
A61Q 5/02 (2006.01)

(52) U.S. Cl. ...................... 510/119; 510/130; 510/342; 510/505; 510/506; 424/70.19; 424/70.22

(58) Field of Classification Search .............. 510/119, 510/130, 342, 505, 506; 424/70.22, 70.19
See application file for complete search history.

(56) References Cited

U.S. PATENT DOCUMENTS 4,303,639 A * 12/1981 Vanlerberghe et al. ........ 424/63

FOREIGN PATENT DOCUMENTS

DE 2432757 A1 1/1976
DE 2651925 A1 5/1978
JP 59-46926 B2 11/1984
JP 63-57698 A 3/1988
JP 1-153610 * 6/1989
JP 1-153610 A 6/1989
JP 2576198 B 11/1996
WO WO 02/07684 A1 1/2002
WO WO 02/17863 A1 3/2002
WO WO 03/008527 A1 1/2003

* cited by examiner

*Primary Examiner*—Brian P Mruk
(74) *Attorney, Agent, or Firm*—Birch, Stewart, Kolasch & Birch, LLP

(57) ABSTRACT

The present invention relates to a surfactant composition containing a composition containing a diol derivative (I) and a surfactant:

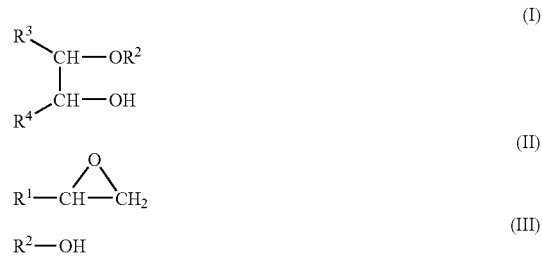

wherein $R^1$ is an alkyl or alkenyl group having 4 to 22 carbons, $R^2$ is an alkyl or alkenyl group having 1 to 18 carbon atoms and one of $R^3$ and $R^4$ is a straight-chain or branched alkyl or alkenyl group having 4 to 22 carbon atoms and derived from $R^1$ and the other is a hydrogen atom.

12 Claims, No Drawings

SURFACTANT COMPOSITION

This Non-provisional application claims priority under 35 U.S.C. § 119(a) on Patent Application No(s). 2003-117938 & 2003-357180 filed in JAPAN on Apr. 23, 2003 & Oct. 17, 2003, the entire contents of which are hereby incorporated by reference.

TECHNICAL FIELD

The present invention relates to a foam-increasing agent for surfactant containing a compound derived from 1,2-epoxyalkane and a surfactant composition containing the foam-increasing agent. The present invention relates to a surfactant composition, preferably used as hair detergent compositions, body detergent compositions, dish detergents or facial cleansing foam.

BACKGROUND ART

Generally, alkanolamide surfactants, betaine surfactants and semi-polar surfactants (e.g., alkyldimethylamine oxide) are known as a thickener or foam-increasing agent and used currently as an auxiliary surfactant in various detergent fields.

Auxiliary surfactants mostly used today are alkanolamide surfactants and amidopropylbetaine.

Also, in WO-A 03/008527, there is a description that a hydroxyalkyl polyhydric ether compound obtained from a 1,2-epoxyalkane and an aliphatic diol is useful as a thickener of a detergent composition.

Also, in JP-A 63-57698, there is a description that an alkane-1,2-diol is formulated in an anionic surfactant to suppress irritation to the skin.

Conventionally, 1,2-alkanediol derivatives are reported as cosmetic bases or as a combination with a cationic surfactant and a polymer endoplasmic reticulum. For example in JP-B 59-46926, there is a description that a 1,2-alkanediol derivative is formulated as a cosmetic base to impart oily nature thereby improving a feel when a detergent containing the derivative is applied. JP-A 1-153610 discloses a hair cosmetic containing a cationic surfactant and a 1,2-alkanediol derivative and describes that the hair cosmetic increases the water-retentivity of the hair after the hair is rinsed and dried and imparts a wet feel and a smooth feel. Also, in JP-B 2576198, there is a description concerning the effects of protecting hairs and imparting a wet feel to hairs by a combination of a polymer endoplasmic reticulum and a 1,2-alkanediol derivative.

DISCLOSURE OF THE INVENTION

The present invention relates to a surfactant composition containing a diol derivative (hereinafter referred to as "component (A)" represented by the formula (I) and a surfactant (hereinafter referred to as "component (B)"):

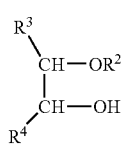

(I)

wherein one of $R^3$ and $R^4$ is a straight-chain or branched alkyl or alkenyl group having 4 to 22 carbon atoms and the other is a hydrogen atom. $R^2$ is a straight-chain or branched alkyl or alkenyl group having 1 to 18 carbons.

Also, the present invention relates to use of the above surfactant composition as a hair detergent use or body detergent. Also, the present invention relates to use of the above component (A) as a surfactant foam-increasing agent.

DETAILED DESCRIPTION OF THE INVENTION

In the above prior art, there is no description as to a function as a foam-increasing agent when a 1,2-alkanediol derivative is used in combination with a surfactant. The surfactant compositions seen in these prior art references all dissatisfy foaming characteristics and quick foaming characteristics.

Alkanolamide surfactants are classified into a monoalkanolamide surfactant and a dialkanolamide surfactant. Although the monoalkanolamide surfactant has an excellent thickening action, it is not said to be a compound having excellent handling characteristics because it has a high melting point. On the other hand, the dialkanolamide surfactant is inferior to the monoalkanolamide surfactant in thickening action and therefore has a difficulty in obtaining a desired viscosity in a reasonable amount though it has high compounding stability.

In the meantime, the amidopropylbetaine surfactant is a superb base from the viewpoint of thickening characteristics and of improving foam properties. However, it has only unsatisfactory foam-increasing characteristics.

Also, because these auxiliary surfactants are nitrogen-containing compounds, they have the disadvantage that many cares must be taken to prevent coloring during the course of the process, coloring of a final product, a deterioration in hue stability during storage and the like.

Therefore, it has been desired to develop a thickener and a foam-increasing agent which contain no nitrogen atom and are used in place of an alkanolamide surfactant or amidopropylbetaine or as an adjuvant for these surfactants.

An alkylglycoside or an alkyl glycidyl ether are usually used as an auxiliary surfactant containing no nitrogen atom. A method of producing these compounds is not simple and several production steps and refining processes are required to produce these compounds. Also, in the case of applying an alkylglycoside to a hair detergent, a strong creak feel is given to hairs and it is therefore difficult to apply it to a hair detergent.

WO-A 03/008527 reveals that in the case of a hydroxyalkyl polyhydric alcohol ether compound, a diol is used as starting material in its production process and it is therefore difficult to obtain a single reaction product. Also, the foaming characteristics are improved unsatisfactorily.

There is nothing described as to an improvement in the foaming characteristics of an anionic surfactant in JP-A 63-57698.

The present invention is to provide a surfactant composition having high foaming characteristics and quick foaming characteristics.

The present invention relates to a foaming agent for surfactant containing a compound derived from a 1,2-epoxyalkane, the foam-increasing agent being a liquid at ambient temperature, having excellent handling characteristics and also being superior in foaming characteristics and low-temperature stability and also to a surfactant composition containing the foam-increasing agent.

The surfactant composition of the present invention produces such an excellent effect as to improve foam-increasing characteristics and quick foaming characteristics.

The present invention includes a surfactant composition containing a composition (hereinafter referred to as "component A") containing a diol derivative (hereinafter referred to as "diol derivative (I)") represented by the formula (I) and obtained by a production method involving a step (1) and a step (2) and a surfactant (hereinafter referred to as "component (B)").

Step 1: A step of supplying a 1,2-epoxyalkane (hereinafter referred to as "1,2-epoxyalkane (II)") represented by the formula (II) and an alcohol (hereinafter referred to as "alcohol (III)") represented by the formula (III) in the following molar ratio: 1,2-epoxyalkane (II)/alcohol (III) =1/1 to 1/20 to react both with each other in the presence of an acid catalyst.

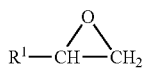
(II)

wherein $R^1$ represents a straight-chain or branched alkyl or alkenyl group having 4 to 22 carbon atoms.

(III)

wherein $R^2$ represents a straight-chain or branched alkyl or alkenyl group having 1 to 18 carbon atoms.

Step 2: A step of removing an unreacted alcohol (III) from the reaction product obtained in Step 1 to obtain a composition comprising the diol derivative (I).

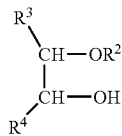
(I)

wherein one of $R^3$ and $R^4$ is a straight-chain or branched alkyl or alkenyl group having 4 to 22 carbon atoms and derived from $R^1$ and the other is a hydrogen atom. $R^2$ has the same meaning as above.

The alkyl or alkenyl group of $R^3$ and $R^4$ has 6 to 12 carbon atoms and $R^2$ is preferably an alkyl or alkenyl group having 1 to 3 carbon atoms.

A surfactant composition containing the component (A) in an amount of 0.5 to 5% by weight in the composition is preferable.

A surfactant composition containing the component (A) in an amount of 3 to 30% by weight based on the surfactant is preferable.

(A) Further, the surfactant is preferably an anionic surfactant.

[Component (A)]

The component (A) in the present invention is obtained using a production method involving the above steps (1) and (2). Examples of the 1,2-epoxyalkane (II) used in the step (1) include 1,2-epoxyoctane, 1,2-epoxydecane, 1,2-epoxydodecane, 1,2-epoxytetradecane, 1,2-epoxyhexadecane, 1,2-epoxyoctadecane, 1,2-epoxyeicosane and 1,2-epoxydocosane. 1,2-epoxyalkanes having 8 to 16 carbon atoms such as 1,2-epoxyoctane, 1,2-epoxydecane, 1,2-epoxydodecane, 1,2-epoxytetradecane and 1,2-epoxyhexadecane are preferable and 1,2-epoxyoctane, 1,2-epoxydecane and 1,2-epoxydodecane are more preferable from the viewpoint of foam-increasing characteristics. 1,2-epoxydecane, 1,2-epoxydodecane and 1,2-epoxytetradecane are preferable from the viewpoint of thickening characteristics.

Examples of the alcohol (III) include methanol, ethanol, n-propyl alcohol, isopropyl alcohol, butyl alcohol, 2-ethylhexyl alcohol, octyl alcohol, decyl alcohol and dodecyl alcohol. Alcohols having 1 to 8 carbon atoms such as methanol, ethanol, n-propyl alcohol, isopropyl alcohol, butyl alcohol and 2-ethylhexyl alcohol from the viewpoint of foam stability and methanol, ethanol, n-propyl alcohol and isopropyl alcohol are more preferable.

The molar ratio (II)/(III) of the 1,2-epoxyalkane (II) to the alcohol (III) to be supplied is 1/1 to 1/20 and preferably 1/1 to 1/10 from the viewpoint of quick foaming characteristics and foaming characteristics.

Although basic catalyst can be used, acid catalyst is more preferable.

Examples of the acid catalyst used in the step (1) include sulfuric acid, hydrochloric acid, nitric acid, phosphoric acid, p-toluenesulfonic acid, m-xylenesulfonic acid and Lewis acid catalysts such as boron trifluoride ether complex. Lewis acid catalysts are preferable. The amount of these acid catalysts is preferably 0.001 to 0.1 mol equivalents and more preferably 0.005 to 0.05 mol equivalents based on the number of mols of 1,2-epoxyalkane (II).

In the step (1), the 1,2-epoxyalkane (II) is preferably reacted with the alcohol (III) at a reaction temperature range from 40 to 60° C. by using a Lewis acid such as boron trifluoride diethyl ether complex as the acid catalyst. Although a solvent is unnecessarily required, a non-polar solvent such as hexane may be used.

The step (2) is a step of removing unreacted alcohol (III) from the reaction product obtained in the step (1). Examples of the removing method include steam distillation and distillation under reduced pressure.

The concentration of the alcohol (III) in the component (A) after the alcohol (III) is removed is preferably 0.5% or less by weight and more preferably 0.1% or less by weight from the viewpoint of odors.

One of $R^3$ and $R^4$ in the diol derivative (I) is a straight-chain or branched alkyl or alkenyl group which has 4 to 22, preferably 6 to 14 and more preferably 6 to 12 carbon atoms and is derived from $R^1$ of the 1,2-epoxyalkane (II) and the other is a hydrogen atom. Also, $R^2$ derived from the alcohol (III) is a straight-chain or branched alkyl or alkenyl group having 1 to 18, preferably 1 to 8 and more preferably 1 to 3 carbon atoms.

The content of the diol derivative (I) in the component (A) is preferably 50 to 99 area % and more preferably 60 to 97 area % from the viewpoint of satisfying both the quick foaming characteristics and foaming characteristics. Also, the component (A) preferably contains a component having a higher molecular weight than the diol derivative (I) such as a dimer of the 1,2-epoxyalkane (II). The content of such a high-molecular weight component is preferably 1 to 50 area % and more preferably 3 to 40 area % in the component (A).

Each content of the diol derivative (I) and the high-molecular weight component in the component (A) is a value measured by gas chromatography in the condition shown in the following examples.

(Component (B))

Examples of the surfactant which is the component (B) include at least one of anionic surfactants, amphoteric surfactants, cationic surfactants, nonionic surfactants, betaine surfactants and the like. A composition containing at least one of, particularly, anionic surfactants is preferable because these anionic surfactants are used for detergents and have excellent foam-increasing characteristics. Also, a composition containing at least one of anionic surfactants and at least one selected from betaine surfactants and nonionic surfactants is more preferable from the viewpoint of the preparation of shampoos and body shampoos.

Examples of the anionic surfactant used in the present invention include such as alkyl sulfates, polyoxyethylene alkyl ether sulfates, alkylbenzene sulfonates, alkyl fatty acid salts, alkyl phosphates, polyoxyethylenealkyl phosphates, acylated amino acid salts and alkylamide ether sulfates.

Examples of the betaine surfactant used in the present invention include amide group-containing betaines such as amidopropyldimethylcarbobetaine and laurylamidopropylbetaine, lauryl acetic acid betaine and lauerylhydroxysulfobetaine.

Examples of the nonionic surfactant used in the present invention alkanolamide surfactants such as monoethanolamide and diethanolamide, alkyl glycosides and alkyl glycidyl ethers.

(Surfactant Composition)

The ratio (A)/(B) by weight of the component (A) to the component (B) to be compounded in the surfactant composition of the present invention is preferably 1/100 to 50/50 and more preferably 5/95 to 25/75.

The content of the component (A) in the surfactant composition of the present invention is preferably 0.1 to 30% by weight and more preferably 0.3 to 20% by weight though it differs depending on the use of the composition and no particular limitation is imposed on it. Also, the content of the component (B) in the surfactant composition of the present invention is preferably 0.1 to 50% by weight and more preferably 0.3 to 30% by weight though it differs depending on the use of the composition and no particular limitation is imposed on it.

In the case of using an anionic surfactant as the component (B), the amount of the anionic surfactant in the surfactant composition of the present invention is preferably 5 to 50% by weight and more preferably 10 to 30% by weight. In the case of combining at least one of anionic surfactants with at least one selected from betaine surfactants and nonionic surfactants, the ratio (weight ratio) of these surfactants to be compounded, namely, (total amount of the betaine surfactant and the nonionic surfactant)/the anionic surfactant is preferably 1/100 to 25/75. The compounding amount of at least one surfactant selected from betaine surfactants and nonionic surfactants in the surfactant composition of the present invention is 0.1 to 10% by weight and more preferably 0.1 to 5% by weight.

The surfactant composition of the present invention may be used as detergent compositions such as hair detergent compositions, body detergent compositions, dish detergents and clothe detergents and preferably used as hair detergent compositions and body detergent compositions.

The surfactant composition of the present invention may be formulated with, besides the above components (A) and (B), components, which are used in usual detergents, for example, moisture retentive agents such as propylene glycol, glycerin and sorbitol; viscosity regulators such as methyl cellulose, polyoxyethylene glycol distearate and ethanol; antibacterial agents such as trichlosane and trichlorocarbane; anti-inflammatory agents such as potassium glycyrrhizin and tocopherol acetate; antidandruff agents such as zinc pyrition and octopyrox; antiseptics such as methyl parabene, butyl parabene, ethyl parabene and propyl parabene; and others including oily components, chelating agents, perfumes, dyes, feeling improvers, salts, pearling agents, scrubbing agents, cold-feel supply agents, ultraviolet absorbers, vegetable extracts and antioxidants according to the need.

Next, the present invention includes a foam-increasing agent for surfactant containing a compound (hereinafter referred to as "compound (1)") represented by the formula (1) and also includes a surfactant composition containing the compound (1) and at least one surfactant.

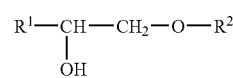

(1)

wherein $R^1$ represents a straight-chain or branched alkyl or alkenyl group having 6 to 21 carbon atoms and $R^2$ represents a straight-chain or branched alkyl or alkenyl group having 1 to 18 carbon atoms.

The structures of the present invention are a foam-increasing agent which will take the place of conventional alkanolamide surfactant or amidopropylbetaine, contains no nitrogen atom, is compounded highly stably and has a high foaming characteristics, and a surfactant composition containing the foam-increasing agent.

It has been found that in this structure, the 1,2-epoxyalkane derivative having the above specified structure has a higher effect on the improvement in foaming characteristics and the effect of promoting foam stability more greatly than alkanolamide surfactants or amidopropylbetaines.

The compound (1) in the present invention may be produced by reacting a 1,2-epoxyalkane (hereinafter referred to as "1,2-epoxyalkane (2)") represented by the formula (3) with an alcohol (hereinafter referred to as "alcohol (3)") represented by the formula (3):

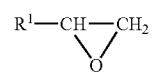

(2)

wherein $R^1$ has the same meaning as above.

 (3)

wherein $R^2$ has the same meaning as above.

Using the aforementioned 1,2-epoxyalkane (2) and alcohol (3), the compound (1) is obtained in the same reaction condition as in the production of the above diol derivative (I).

In the production of the compound (1), the reaction also proceeds even if a basic catalyst such as a sodium methylate or a tertiary amine, a quaternary salt catalyst such as tetrabutylammonium bromide or an acid catalyst such as sulfuric acid and phosphoric acid is used.

The molar ratio of the 1,2-epoxyalkane (2) to the alcohol (3), namely, (3):(2) is in a range from preferably 1:1 to 10:1 and more preferably 1:1 to 3:1 from the viewpoint of controlling the amount of dimers of the 1,2-epoxyalkane (2) and from an economical point of view though no particular limitation is imposed on it. It is preferable to remove an excess of the alcohol (3) by steam distillation or distillation under reduced pressure after the reaction is finished.

The foam-increasing agent of the present invention contains the compound (1) as an essential component. The foam-increasing agent may contain, beside the compound (1), a dimer of the 1,2-epoxyalkane (2) and the like, which dimer is obtained by the above reaction in the production the compound (1) to the extent that it is no hindrance to practical use. The content of the compound (1) in the foam-increasing agent of the present invention is preferably 50 to 100% by weight and more preferably 70 to 100% by weight.

The compound (1) in the present invention has the effect of remarkably improving foaming characteristics when a surfactant is compounded.

The surfactant composition of the present invention contains the compound (1) and at least one surfactant. As the surfactant, at least one of an anionic surfactant, amphoteric surfactant, cationic surfactant, nonionic surfactant, betaine surfactant and the like may be used. An anionic surfactant is preferable.

Although the content of the compound (1) in the surfactant composition of the present invention differs depending on the use of the composition and no particular limitation is imposed on the content, the content is preferably 0.1 to 50% by weight, more preferably 0.1 to 30% by weight and even more preferably 0.3 to 20% by weight. Although the ratio by weight of the compound (1) to the surfactant to be compounded differs depending on the use of the composition and no particular limitation is imposed on the ratio, the ratio of compound (1)/surfactant is preferably 1/99 to 70/30 and more preferably 3/97 to 50/50.

The surfactant composition of the present invention may be used as dish detergents and cloth detergents in household fields and detergents for personal care use such as hair detergents and body detergents. Also, a two-component system containing the compound (1) and various surfactants may be used or the compound (1) may be added to combination of these various surfactants, depending on how to use the detergent.

The present invention makes it possible to provide a foam-increasing agent for surfactant which include no nitrogen atom, is a liquid at ambient temperature, has excellent handling characteristics and is superior in thickening effect, foaming characteristics and low-temperature stability.

EXAMPLES

In the following production examples, the condition of gas chromatographic analysis of a diol derivative-containing composition is as follows:

Column: Ultra ALLOY (trademark), 15 m×0.25 mmϕ, film thickness: 0.15 μm

Manufacturer: HEWLETT PACKARD HP4890

Measuring condition: Initial temperature 60° C., two minutes at 60° C., temperature rise rate 10° C./min (up to 320° C.), 15° C./min (320 to 350° C.)

Production Example 1

A 1 L reactor equipped with a thermometer, a stirrer, a nitrogen blowing tube and a reflux condenser was charged with 64 g (2 mol) of methanol and 2 g of boron trifluoride diethyl ether complex and then the mixture was raised to 60° C. Then, 128.2 g (1 mol) of 1,2-epoxyoctane was added dropwise to the mixture over one hour and the resulting mixture was kept as it was for 3 hours. The reaction was terminated just after confirming that 1,2-epoxyoctane left unreacted was less than 1% by gas chromatography and then the reaction mixture was cooled. Thereafter, the reaction mixture was transferred to a 1 L Herz equipped with a nitrogen blowing tube, a vacuuming device and a fraction condenser. After the mixture was heated to 30° C., nitrogen was blown under a pressure of 40 kPa to remove methanol thereby obtaining a diol derivative-containing composition.

The obtained diol derivative-containing composition contained 68% (area) of 2-hydroxyoctyl methyl ether and 32% (area) of components having a higher molecular weight than 2-hydroxyoctyl methyl ether as a result of gas chromatographic analysis.

Production Example 2

A diol derivative-containing composition was obtained in the same manner as in Production Example 1 except that the amount of methanol to be charged was changed to 256 g (8 mol).

The obtained diol derivative-containing composition contained 94% (area) of 2-hydroxyoctyl methyl ether and 6% (area) of a component having a higher molecular weight than 2-hydroxyoctyl methyl ether as a result of gas chromatographic analysis.

Production Example 3

A diol derivative-containing composition was obtained in the same manner as in Production Example 1 except that 156.2 g (1 mol) of 1,2-epoxydecane was added dropwise over one hour in place of 1,2-epoxyoctane.

The obtained diol derivative-containing composition contained 69% (area) of 2-hydroxydecyl methyl ether and 31% (area) of components having a higher molecular weight than 2-hydroxydecyl methyl ether as a result of gas chromatographic analysis.

Production Example 4

A diol derivative-containing composition was obtained in the same manner as in Production Example 1 except that 184.3 g (1 mol) of 1,2-epoxydodecane was added dropwise over one hour in place of 1,2-epoxyoctane.

The obtained diol derivative-containing composition contained 70% (area) of 2-hydroxydodecyl methyl ether and 30% (area) of components having a higher molecular weight than 2-hydroxydodecyl methyl ether as a result of gas chromatographic analysis.

Comparative Production Example 1

A diol derivative-containing composition was obtained in the same manner as in Production Example 1 except that the amount of methanol to be charged was altered to 800 g (25 mol).

The obtained diol derivative-containing composition contained 99.3% (area) of 2-hydroxyoctyl methyl ether and 0.7% (area) of components having a higher molecular weight than 2-hydroxyoctyl methyl ether as a result of gas chromatographic analysis.

Examples 1 to 4 and Comparative Examples 1 to 5

The diol derivative-containing compositions obtained in Production Examples 1 to 4 and Comparative Production Example 1, the following comparative products and a sodium polyoxyethylene(2) lauryl ether sulfate (AES) were used to prepare surfactant compositions shown in Table 1. With regard to these compositions, the quick foaming characteristics and the amount of foam were examined in the following methods. The results are shown in Table 1.

<Comparative Products>
MEA: Coconut oil fatty acid monoethanolamide
DEA: Palm kernel oil fatty acid diethanolamide
CAPB: Coconut oil fatty acid amidopropylbetaine <Test Method of Quick Foaming Characteristics>

Using a quick foaming tester having the structure shown in FIG. 1 of JP-A 10-73584, the time required until the amount of foam reached 250 mL was measured in the presence of 0.2 mL of pseudo-sebum in the following conditions and procedures by using 1.0 mL of each surfactant composition to evaluate the composition according to the following four ranks.

| Condition | |
|---|---|
| Amount of hair | 30 g |
| Amount of water to be added | 32 g |
| Surfactant composition | 1.0 mL |
| Amount of pseudo-sebum | 0.2 mL (purified lanolin: 95% and oleic acid: 5%) |

Procedure

1) As described in JP-A 10-73584, Paragraph No. 0053, 30 g of 90 mm hairs were transplanted in a circular plate having a diameter of about 160 mm. This circular plate was set to a cylindrical container having a diameter of 160 mm and a height of 22 mm. The lid of this cylindrical container is provided with three cylindrical first projections having a diameter of 15 mm and a height of 12 mm and nine second projections having a length of 10 mm, a width of 2 mm and a height of 12 mm.

2) The hair was washed twice with a commercially available shampoo containing primarily an anionic surfactant and then about 2 g of a commercially available conditioner primarily containing a cationic surfactant and a higher alcohol was applied to the hair, followed by sufficiently rinsing the hair with warm water.

3) 0.2 mL of pseudo-sebum was added in the cylindrical container, which was then rotated at 60 rpm.

4) The surfactant composition in an amount of 1.0 mL measured using a syringe was added to the cylindrical container and the measuring of the time was started at the same time when the components were added.

5) The time required until the amount of foam in a weigher installed on the upper portion of cylindrical container reached 250 mL was measured.

Evaluation Standard

⊙: Less than 60 seconds (very good).
○: 60 seconds or more and less than 120 seconds (good)
Δ: 120 seconds or more and less than 180 seconds (normal)
×: 180 seconds or more (inferior)

<Test Method of the Amount of Foam>

20 g of the hairs (length: 20 cm) of a Japanese woman were bundled and 1.0 mL of each surfactant composition was applied evenly to the hair bundle by using 40° C. city water. Then, the hair bundle was rubbed by hands for 30 seconds to wash. The amount of foam was evaluated by 5 panelists according to the following standard and the results of the evaluation made by 5 panelists were averaged.

⊙: Amount of foam is very large.
○: Amount of foam is large.
Δ: Amount of foam is normal.
×: Amount of foam is small.

TABLE 1

| | | Example | | | | Comparative example | | | | |
|---|---|---|---|---|---|---|---|---|---|---|
| | | 1 | 2 | 3 | 4 | 1 | 2 | 3 | 4 | 5 |
| Surfactant composition (weight-%) | Diol derative-containing composition in production example 1 | 3 | | | | | | | | |
| | Diol derative-containing composition in production example 2 | | 3 | | | | | | | |
| | Diol derative-containing composition in production example 3 | | | 3 | | | | | | |
| | Diol derative-containing composition in production example 4 | | | | 3 | | | | | |
| | Diol derative-containing composition in comparative production example 1 | | | | | | 3 | | | |
| | MEA | | | | | 3 | | | | |
| | DEA | | | | | | | 3 | | |
| | CAPB | | | | | | | | 3 | |
| | AES | 17 | 17 | 17 | 17 | 17 | 17 | 17 | 17 | 20 |
| | Purified water | Balance | Balance | Balance | Balance | Balance | Balance | Balance | Balance | Balance |
| Result of test | Quick foaming characteristics | ○ | ○ | ⊙ | ⊙ | × | ○ | ○ | ○ | × |
| | Amount of foam | ⊙ | ⊙ | ⊙ | ⊙ | ○ | ○ | Δ | ○ | × |

Formulation Examples 1 to 4 of detergent compositions including the diol derivative-containing compositions obtained in Production Examples 1 to 4 are shown below.

Formulation Example 1: Hair Detergent

A hair detergent having the composition shown in Table 2 was prepared. The hair detergent had a moderate viscosity and exhibited superior quick foaming characteristics and sufficient foam-increasing characteristics. The detergent gave a creaky feel to hairs during both washing and rinsing, allowed fingers to pass through hairs very smoothly and gave very fresh washing finish to hairs.

TABLE 2

| Composition | weight-% |
| --- | --- |
| Sodium polyoxyethylene(2) lauryl ether sulfate | 15.0 |
| Diol derivative-containing composition of production example 1 | 3.0 |
| Coconut oil fatty acid amidopropylbetaine*[1] | 0.6 |
| Ethylene glycol distearate | 2.0 |
| Polyoxyethylene hydrogenated caster oil (60 mol of EO is added) | 0.5 |
| Cationic cellose*[2] | 0.3 |
| Silicone | Proper amount |
| Antioxidant | Proper amount |
| Chelating agent | Proper amount |
| Anticeptic | Proper amount |
| Perfume | Proper amount |
| Dye | Proper amount |
| Purified water | Balance |

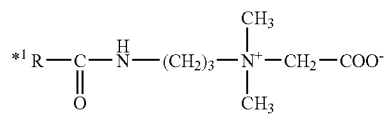

(R: Derived from coconut oil fatty acid)
*[2]Ucare polymer JR-400 (produced by Amerchol Corporation)

Formulation Example 2: Hair Detergent

A hair detergent having the composition shown in Table 3 was prepared. The hair detergent had a moderate viscosity and exhibited superior quick foaming characteristics and sufficient foam-increasing characteristics and produced sturdy and creamy foam. The detergent gave no creaky feel to hairs during both washing and rinsing, allowed fingers to pass through hairs very smoothly and gave very fresh washing finish to hairs.

TABLE 3

| Composition | weight-% |
| --- | --- |
| Sodium polyoxyethylene (2) lauryl ether sulfate | 15.0 |
| Diol derivative-containing composition of production example | 3.0 |
| Coconut oil fatty acid amidopropylbetaine*[1] | 0.6 |
| Ethylene glycol distearate | 2.0 |
| Polyoxy ethylene hydrogenated caster oil (60 mol of EO is added) | 0.5 |
| Cationic cellulose*[2] | 0.3 |
| Silicone | Proper amount |
| Antioxidant | Proper amount |
| Chelating agent | Proper amount |
| Anticeptic | Proper amount |
| Perfume | Proper amount |
| Dye | Proper amount |
| Purified water | Balance |

*[1] and *[2] are same as Table 2

Formulation Example 3: Body Detergent

A body detergent having the composition shown in Table 4 was prepared. When this body detergent was used for washing hands, it produced sturdy and creamy foam and gave very fresh washing finish to the body.

TABLE 4

| Composition | weight-% |
| --- | --- |
| Potassium coconut oil fatty acid salt | 9 |
| Potassium laurate | 6.8 |
| Potassium myristate | 2.3 |
| Diol derivative-containing composition of product | 3.0 |
| Coconut oil fatty acid amidopropylbetaine*[1] | 0.6 |
| Laurylhydroxysulfobetaine*[3] | 1.5 |
| Sorbitol | 3.5 |
| Concenrated glycerin for cosmetic | 5.0 |
| Cationic cellulose*[2] | 0.5 |
| Ethylene glycol distearate | 2.0 |
| Antioxidant | Proper amount |
| Chelating agent | Proper amount |
| Anticeptic | Proper amount |
| Perfume | Proper amount |
| Dye | Proper amount |
| Purifie water | Blance |

*[1] and *[2] are same as those in Table 2

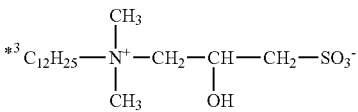

Formulation Example 4: Body Detergent

A body detergent having the composition shown in Table 5 was prepared. When this body detergent was used for washing hands, it produced sturdy and creamy foam and gave very fresh washing finish to the body.

TABLE 5

| Composition | Weight-% |
| --- | --- |
| Potassium coconut fatty oil acid | 9 |
| Potassium laurate | 6.8 |
| Potassium myristate | 2.3 |
| Diol derivative-containing composition of production example | 3.0 |
| Coconut oil fatty acid amidopropylbetaine*[1] | 0.6 |
| Laurylhydroxysulfobetaine*[3] | 1.5 |
| Sorbitol | 3.5 |
| Concenrated glycerin for cosmetic | 5.0 |
| Cationic cellulose*[2] | 0.5 |
| Ethylene glycol distearate | 2.0 |
| Antioxidant | Proper amount |
| Chelating agent | Proper amount |
| Anticeptic | Proper amount |
| Perfume | Proper amount |
| Dye | Proper amount |
| Purified water | Proper amount |

*[1]and *[2]are the same as table 2
*[3]is same as Table 4

Production Example 5

A 1 L reactor equipped with a thermometer, a stirrer, a nitrogen blowing tube and a reflux condenser was charged with 64 g (2 mol) of methanol and 2 g of boron trifluoride diethyl ether complex and then the mixture was raised to 60° C. Then, 128.2 g (1 mol) of 1,2-epoxyoctane was added dropwise to the mixture over one hour and the resulting mixture was kept as it was for 3 hours. The reaction was terminated just after confirming that 1,2-epoxyoctane left unreacted was less than 1% by gas chromatography and then the reaction mixture was cooled. Thereafter, the reaction mixture was transferred to a 1 L Herz equipped with a nitrogen blowing tube, a vacuuming device and a fraction condenser. After the mixture was heated to 30° C., nitrogen was blown under a pressure of 40 kPa to remove methanol thereby obtaining 2-hydroxyoctyl methyl ether.

Production Example 6

The same reactor that was used in Production Example 5 was charged with 64 g (2 mol) of methanol and 2 g of boron trifluoride diethyl ether complex and then the mixture was raised to 60° C. Then, 156.2 g (1 mol) of 1,2-epoxydecane was added dropwise to the mixture over one hour and the resulting mixture was kept as it was for 3 hours. The reaction was terminated just after confirming that 1,2-epoxydecane left unreacted was less than 1% by gas chromatography and then the reaction mixture was cooled. Thereafter, methanol was removed in the same manner as in Production Example 5 to obtain 2-hydroxydecyl methyl ether.

Production Example 7

The same reactor that was used in Production Example 5 was charged with 64 g (2 mol) of methanol and 2 g of boron trifluoride diethyl ether complex and then the mixture was raised to 60° C. Then, 184.3 g (1 mol) of 1,2-epoxydodecane was added dropwise to the mixture over one hour and the resulting mixture was kept as it was for 3 hours. The reaction was terminated just after confirming that 1,2-epoxydodecane left unreacted was less than 1% by gas chromatography and then the reaction mixture was cooled. Thereafter, methanol was removed in the same manner as in Production Example 5 to obtain 2-hydroxydodecyl methyl ether.

Production Example 8

The same reactor that was used in Production Example 5 was charged with 64 g (2 mol) of methanol and 2 g of boron trifluoride diethyl ether complex and then the mixture was raised to 60° C. Then, 212.3 g (1 mol) of 1,2-epoxytetradecane was added dropwise to the mixture over one hour and the resulting mixture was kept as it was for 3 hours. The reaction was terminated just after confirming that 1,2-epoxytetradecane left unreacted was less than 1% by gas chromatography and then the reaction mixture was cooled. Thereafter, methanol was removed in the same manner as in Production Example 5 to obtain 2-hydroxytetradecyl methyl ether.

Production Example 9

The same reactor that was used in Production Example 5 was charged with 92 g (2 mol) of ethanol and 2 g of boron trifluoride diethyl ether complex and then the mixture was raised to 60° C. Then, 156.2 g (1 mol) of 1,2-epoxydecane was added dropwise to the mixture over one hour and the resulting mixture was kept as it was for 3 hours. The reaction was terminated just after confirming that 1,2-epoxydecane left unreacted was less than 1% by gas chromatography and then the reaction mixture was cooled. Thereafter, the reaction mixture was transferred to a 1 L Herz equipped with a nitrogen blowing tube, a vacuuming device and a fraction condenser. After the mixture was heated to 40° C., nitrogen is blown under a pressure of 40 kPa to remove ethanol thereby obtaining 2-hydroxydecyl ethyl ether.

Production Example 10

The same reactor that was used in Example 5 was charged with 92 g (2 mol) of methanol and 2 g of boron trifluoride diethyl ether complex and then the mixture was raised to 60° C. Then, 184.3 g (1 mol) of 1,2-epoxydodecane was added dropwise to the mixture over one hour and the resulting mixture was kept as it was for 3 hours. The reaction was terminated just after confirming that 1,2-epoxydodecane left unreacted was less than 1% by gas chromatography and then the reaction mixture was cooled. Thereafter, methanol was removed in the same manner as in Production Example 9 to obtain 2-hydroxydodecyl ethyl ether.

Example 5

The compounds obtained in Production Examples 5 to 10 and the following Comparative Product and a sodium polyoxyethylene(3) lauryl ether sulfate (AES) were used to prepare surfactant compositions shown in Table 6. With regard to these compositions, a foaming test was made in the following methods. The results are shown in Table 6.

<Comparative Products>
LAPB: Lauroylamidopropyldimethylcarbobetaine
DEA: Coconut oil fatty acid diethanolamide
MEA: Coconut oil fatty acid monoethanolamide
DGE: Decyl glyceryl ether <Foaming Test>
The test was made by measuring in the following condition according to a Ross-Miles method.
Concentration of a surfactant composition: 0.2% by weight
Temperature 40° C.
Hardness 4° DH
pH 6.8

TABLE 6

| | | Product of the present invention | | | | | | Comparative product | | | |
|---|---|---|---|---|---|---|---|---|---|---|---|
| | | 1 | 2 | 3 | 4 | 5 | 6 | 1 | 2 | 3 | 4 |
| Surfactant composition (weight-%) | Compound in production example 5 | 0.75 | | | | | | | | | |
| | Compound in production example 6 | | 0.75 | | | | | | | | |
| | Compound in production example 7 | | | 0.75 | | | | | | | |
| | Compound in production example 8 | | | | 0.75 | | | | | | |
| | Compound in production example 9 | | | | | 0.75 | | | | | |
| | Compound in production example 10 | | | | | | 0.75 | | | | |
| | LAPB | 3.75 | 3.75 | 3.75 | 3.75 | 3.75 | 3.75 | 6 | 3.75 | 3.75 | 3.75 |
| | DEA | | | | | | | | 0.75 | | |

TABLE 6-continued

|  | Product of the present invention | | | | | | Comparative product | | | |
| --- | --- | --- | --- | --- | --- | --- | --- | --- | --- | --- |
|  | 1 | 2 | 3 | 4 | 5 | 6 | 1 | 2 | 3 | 4 |
| MEA |  |  |  |  |  |  |  | 0.75 |  |  |
| DGE |  |  |  |  |  |  |  |  |  | 0.75 |
| AES | 10.5 | 10.5 | 10.5 | 10.5 | 10.5 | 10.5 | 14 | 10.5 | 10.5 | 10.5 |
| Purifie water | Balance (amount to be a total of 100% by weight) | | | | | | | | | |
| Amount of foam (mm) | 287 | 275 | 278 | 276 | 268 | 270 | 240 | 250 | 251 | 250 |

Example 6

The compounds obtained in Production Examples 5 to 10 or the aforementioned LAPB, DEA and MEA were used as auxiliary surfactants and AES was used as a surfactant to prepare surfactant compositions in which the total concentration of the surfactants was 20% by weight and the ratio (surfactant/auxiliary surfactant) (weight ratio) was 17/3. Each viscosity of these compositions was measured in the following condition. The results are shown in Table 7.
<Viscosity Measuring Condition>
Measuring pH: 7.0
Measuring temperature: 25° C.
Viscometer: B-type viscometer

TABLE 7

| Auxiliary surfactant | Viscosity (mPa · s) |
| --- | --- |
| Compound in production example 5 | 290 |
| Compound in production example 6 | 8800 |
| Compound in production example 7 | 15000 |
| Compound in production example 8 | 7800 |
| Compound in production example 9 | 5500 |
| Compound in production example 10 | 7500 |
| LAPB | 1440 |
| DEA | 140 |
| MEA | 450 |

Example 7

The same reactor that was used in Example 1 was charged with 64 g (MW: 32, 2 mol) of methanol and 2 g of sodium methylate (CH3ONa) and then the mixture was raised to 60° C. Then, 156.2 g (MW: 156.2, 1 mol) of 1,2-epoxydecane was added dropwise to the mixture over one hour and the resulting mixture was kept as it was for 8 hours. The reaction was terminated just after confirming that 1,2-epoxydecane left unreacted was less than 1% by gas chromatography and then the reaction mixture was cooled.

Example 1 to 7 of Table 8 correspond to Production Example 5 to 11 of Table 7, respectively. Comparative Example 1 to 3 of Table 8 correspond to LAPB, DEA and MEA of Table 7, respectively.

TABLE 8

|  | Viscosity (mPa · s) | Amount of foam (mm) |
| --- | --- | --- |
| Example 1 | 290 | 287 |
| Example 2 | 8800 | 275 |
| Example 3 | 15000 | 278 |
| Example 4 | 7800 | 276 |
| Example 5 | 5500 | 268 |
| Example 6 | 7500 | 270 |
| Example 7 | 275 | 276 |
| Comparative example 1 | 1440 | 240 |
| Comparative example 2 | 140 | 250 |
| Comparative example 3 | 450 | 251 |

The invention claimed is:

1. A surfactant composition comprising a diol derivative (hereinafter referred to as "component (A)") represented by the formula (I) and at least one anionic surfactant (hereinafter referred to as "component (B)"):

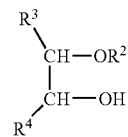
(I)

wherein one of $R^3$ and $R^4$ is a straight-chain or branched alkyl or alkenyl group having 4 to 22 carbon atoms and the other is a hydrogen atom and $R^2$ is methyl or ethyl.

2. The surfactant composition according to claim 1, wherein the component (A) is a diol derivative-containing composition obtained in a production method comprising a step (1) and a step (2):
   step 1: a step of supplying a 1,2-epoxyalkane (hereinafter referred to as "1,2-epoxyalkane (II)") represented by the formula (II) and an alcohol (hereinafter referred to as "alcohol (III)") represented by the formula (III) in the following molar ratio: 1,2-epoxyalkane (II)/alcohol (III)=1/1 to 1/20 to react both with each other in the presence of an acid catalyst:

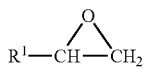
(II)

wherein $R^1$ represents a straight-chain or branched alkyl or alkenyl group having 4 to 22 carbon atoms;

(III)

wherein $R^2$ represents an alkyl group having 1 or 2 carbon atoms: and
   step 2: a step of removing an unreacted alcohol (III) from the reaction product obtained in the step 1 to obtain a composition comprising the diol derivative represented by the formula (I).

3. The surfactant composition according to claim 1 or 2, wherein the component (B) further comprises at least one surfactant selected from a betaine surfactant and a nonionic surfactant.

4. The surfactant composition according to any one of claims 1, 2 or 3, wherein the ratio by weight of the component (A) to the component (B), namely (A)/(B), is 1/100 to 50/50.

5. A hair detergent comprising the surfactant composition as claimed in claim 1.

6. A body detergent comprising the surfactant composition as claimed in claim 1.

7. The surfactant composition according to claim 1 or 2, wherein the component (A) is a compound represented by the formula (1):

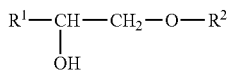
(1)

wherein $R^1$ is a straight-chain or branched alkyl or alkenyl group having 6 to 21 carbon atoms and $R^2$ is an alkyl group having 1 or 2 carbon atoms.

8. The surfactant composition according to claim 1 or 2, wherein the alkyl or alkenyl group of $R^3$ and $R^4$ has 6 to 12 carbon atoms.

9. The surfactant composition according to claim 1 or 2, wherein the content of the component (A) in the composition is 0.5 to 5% by weight.

10. The surfactant composition according to claim 1, wherein the content of the component (A) is 3 to 30% by weight based on the anionic surfactant.

11. The surfactant composition according to claim 1 or 2, wherein the component (A) comprises a component having a higher molecular weight than the diol derivative (I) including a dimer of the 1,2-epoxyalkane (II).

12. A body or hair detergent comprising component (A) as described in claim 1 or 2.

* * * * *